US00PP08025P

United States Patent [19]

Meilland

[11] Patent Number: Plant 8,025

[45] Date of Patent: Nov. 10, 1992

[54] ROSE PLANT—MEICORVAL VARIETY

[75] Inventor: Alain A. Meilland, Antibes, France

[73] Assignee: The Conard-Pyle Company, West Grove, Pa.

[21] Appl. No.: 717,494

[22] Filed: Jun. 19, 1991

[51] Int. Cl.[5] ..... A01H 5/00

[52] U.S. Cl. ..... Plt./29

[58] Field of Search ..... Plt./22, 28, 29

*Primary Examiner*—Howard J. Locker

*Attorney, Agent, or Firm*—Burns, Doane, Swecker & Mathis

[57] ABSTRACT

A new and distinct variety of Polyantha rose plant is provided which abundantly forms attractive semi-double very long lasting blossoms which are an attractive currant red widely suffused with cardinal red. The plant exhibits a semi-erect growth habit and forms very vigorous vegetation. Excellent aptitude to forcing is exhibited and the plant is particularly well suited for cut flower production. Additionally, the plant exhibits very good disease resistance.

1 Drawing Sheet

SUMMARY OF THE INVENTION

The new variety of Polyantha rose plant was created by artificial pollination wherein two parents were crossed which previously had been studied in the hope that they would contribute the desired characteristics. The female parent (i.e., the seed parent) of the new variety was the Meikans variety (nonpatented in the United States). The male parent (i.e., the pollen parent) was the Meichevil variety (U.S. Plant Pat. No. 7,334). The parentage of the new variety can be summarized as follows:

Meikans × Meichevil.

The seeds resulting from the above pollination were sown and 86 small plants were obtained which were physically and biologically different from each other. Selective study resulted in the identification of a single plant of the new variety.

It was found that the new variety of Polyantha rose plant of the present invention possesses the following combination of characteristics:

(a) forms in abundance attractive very long lasting semi-double blossoms which are current red widely suffused with cardinal red in coloration,
(b) forms bronze green adult wood,
(c) forms blossoms which are lacking in fragrance,
(d) exhibits very vigorous vegetation,
(e) exhibits a semi-erect growth habit,
(f) exhibits an excellent aptitude to be forced and is particularly suited for cut flower production, and
(g) is not particularly affected by cryptogamic diseases.

The new variety well meets the needs of the horticultural industry and is particularly well suited for use in the production of attractive cut flowers.

The new variety has been found to undergo asexual propagation by a number of routes, including budding, grafting, cuttage, etc. Asexual propagation by the above mentioned methods as performed in France has shown that the characteristics of the new variety are strictly transmissible from one generation to another.

The new variety has been named the Meicorval variety.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were two years of age and were observed during February while budded on *Rose indica* understock and growing in greenhouses at Cap d' Antibes, France.

DETAILED DESCRIPTION

Figures 1, 2, 3, 4, 5, 6, 7, 8, 9, 10, 11, 12, 13, 14, 15, 16:
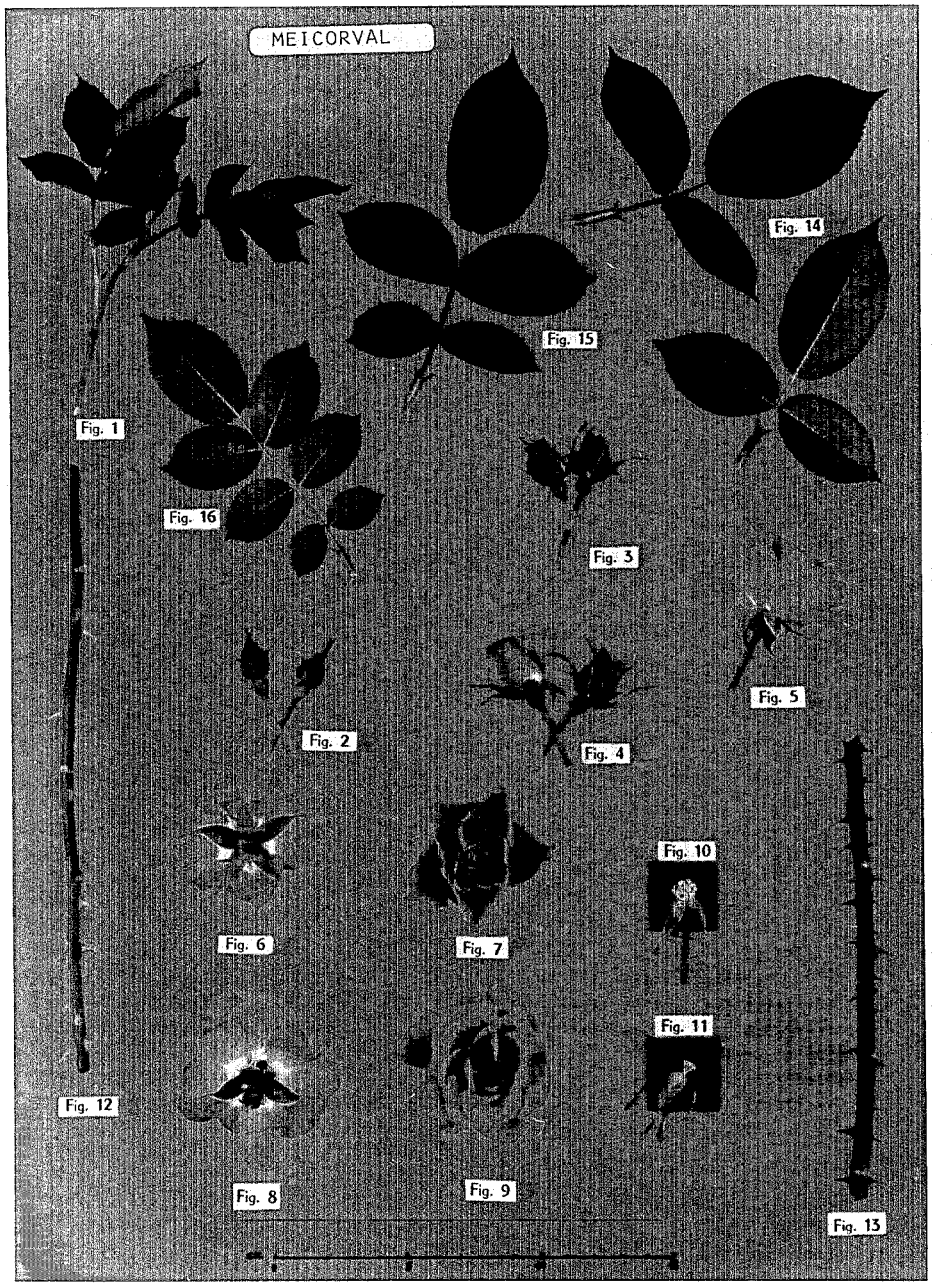
FIG. 1 illustrates a specimen of a young shoot.
FIG. 2 illustrates specimens of two floral buds before the opening of the sepals.
FIG. 3 illustrates specimens of two floral buds at the opening of the sepals.
FIG. 4 illustrates specimens of two floral buds at the opening of the petals.
FIG. 5 illustrates a specimen of a flower in the course of opening.
FIG. 6 illustrates a specimen of an open flower—plan view—reverse.
FIG. 7 illustrates a specimen of an open flower—plan view—obverse.
FIG. 8 illustrates a specimen of a fully open flower—plan view—reverse.
FIG. 9 illustrates a specimen of a fully open flower—plan view—obverse.
FIG. 10 illustrates a specimen of a floral receptacle showing the arrangement of the stamens and pistils.
FIG. 11 illustrates a specimen of a floral receptacle showing the arrangement of the pistils (stamens removed)
FIG. 12 illustrates a specimen of a flowering stem.
FIG. 13 illustrates a specimen of a main branch.
FIG. 14 illustrates specimens of leaves with three leaflets—plan view—upper surface (top) and lower surface (bottom)
FIG. 15 illustrates a specimen of a leaf with five leaflets—plan view—upper surface.
FIG. 16 illustrates a specimen of a leaf with seven leaflets—plan view—under surface.

The chart used in the identification of the colors is that of The Royal Horticultural Society (R.H.S. Colour Chart). The description is based on the observation of two year old plants made during February while budded on *Rose indica* understock and growing in greenhouses at Cap d' Antibes, France. The coloration in common terms precedes reference to the chart.

Class: Polyantha.

Plant:

*Height.*—When plants are cut to a height of 85 cm., flowering stems are produced having a length of approximately 40 to 60 cm. The total plant height when grown in fields at Wasco, Calif., at the end of one growing season is approximately 85 to 95 cm.

*Habit.*—Semi-erect.

Branches:

*Color.*—Young stems: light green, Yellow-Green Group 146C. Adult wood: bronze green, Yellow-Green Group 146A.

*Thorns.*—Size: small to average. Quantity: moderately numerous. Color: pinkish green on young stems and greenish changing to tan on mature wood.

Leaves:

*Stipules.*—Adnate, pectinate, wide and linear.

*Petioles.*—Upper surface: striped reddish brown on young foliage and medium green on adult foliage with more or less glandular edges. Under surface: light green, smooth.

*Leaflets.*—Number: 3, 5 (most often), and 7. Shape: elliptic. Serration: simple and regular. Texture: consistent. General appearance: dense, semi-matte foliage. Color (young foliage): Upper surface: dark green, Green Group 137A. Under surface: medium greyish green, Greyed-Green Group 191A. Color (adult foliage): Upper surface: dark green, Green Group 139A. Under surface: medium green, Green Group 138A.

Inflorescence:

*Number of flowers.*—Often 1 to 6 blooms per stem, and most commonly 3 to 5 blooms per stem.

*Peduncle.*—Long, straight, fairly rigid, sometimes curled, and bears numerous glandular acicules. The length is approximately 5.5 to 8 cm. on average.

*Sepals.*—Upper surface: tomentose, greenish in coloration. Under surface: light green, glandular, with the outer sepals being only slightly appendiculated.

*Buds.*—Shape: conical. Length: approximately 2 cm. on average. Size: medium. Color upon opening: Upper surface: currant red, Red Group 46A. Under surface: light cardinal red, Red Group 53A.

*Flower.*—Shape: cup-like with parallel sides, semi-double. Diameter: approximately 6 to 6.5 cm. on average. Color (when opening begins): Upper surface: currant red, Red Group 46A, widely suffused with cardinal red, Red Group 53A. Under surface: light cardinal red, Red Group 53C, lighter towards the base, and near white at the point of attachment. Color (when blooming): Upper surface: currant red, Red Group 46A, widely suffused with cardinal red, Red Group 53C. Under surface: cardinal red, Red Group 53C, becoming lighter towards the base, and near white at the point of attachment. Color (at end of opening): Upper surface: cardinal red, Red Group 53C, and lightly suffused with light currant red, Red Group 46C. Under surface: light cardinal red, Red Group 53C, suffused with rose bengel, Red-Purple Group 57C, and turning near white at the point of attachment. Fragrance: none. Lasting quality: very long lasting either on the plant or when cut and placed in a vase. Petal number: approximately 17 to 23 on average. Texture: consistent. Petal drop: fairly good. Stamen number: approximately 77 on average. Anthers: normal, located below or at the same level as the stigmas. Filaments: greenish straw in coloration, of irregular heights. Pistils: approximately 35 on average. Stigmas: normal, straw colored. Styles: greenish in coloration, more or less twisted, and irregular in heights. Receptacles: medium green in coloration, and in longitudinal section it is in the shape of a pitcher.

Development:

*Vegetation.*—Very vigorous.

*Blooming.*—Very abundant.

*Resistance to diseases.*—Very good.

*Aptitude to forcing.*—Excellent.

I claim:

1. A new and distinct variety of Polyantha rose plant characterized by the following combination of characteristics:

(a) forms in abundance attractive very long lasting semi-double blossoms which are currant red widely suffused with cardinal red in coloration,
(b) forms bronze green adult wood,
(c) forms blossoms which are lacking in fragrance,
(d) exhibits very vigorous vegetation,
(e) exhibits a semi-erect growth habit,
(f) exhibits an excellent aptitude to be forced and is particularly suited for cut flower production, and
(g) is not particularly affected by cryptogamic diseases;

substantially as herein shown and described.

* * * * *

MEICORVAL